United States Patent
Lapierre et al.

(10) Patent No.: US 11,020,400 B2
(45) Date of Patent: Jun. 1, 2021

(54) TETRAHYDROPYRANYL AMINO-PYRROLOPYRIMIDINONE AND METHODS OF USE THEREOF

(71) Applicant: ArQule, Inc., Burlington, MA (US)

(72) Inventors: Jean-Marc Lapierre, Pelham, NH (US); Sudharshan Eathiraj, Shrewsbury, MA (US); Nivedita Namdev, Westford, MA (US); Brian Schwartz, Woodbridge, CT (US); Yusuke Ota, Tokyo (JP); Takayuki Momose, Tokyo (JP); Tomoyuki Tsunemi, Tokyo (JP); Hiroaki Inagaki, Tokyo (JP); Kiyoshi Nakayama, Tokyo (JP)

(73) Assignee: ArQule, Inc., Burlington, MA (US)

( * ) Notice: Subject to any disclaimer, the term of this patent is extended or adjusted under 35 U.S.C. 154(b) by 0 days.

(21) Appl. No.: 16/672,971

(22) Filed: Nov. 4, 2019

(65) Prior Publication Data
US 2020/0061071 A1    Feb. 27, 2020

Related U.S. Application Data

(60) Continuation of application No. 16/291,224, filed on Mar. 4, 2019, which is a division of application No. 15/448,719, filed on Mar. 3, 2017, now Pat. No. 10,245,263, which is a continuation of application No. 14/757,745, filed on Dec. 23, 2015, now Pat. No. 9,630,968.

(51) Int. Cl.
*A61K 31/519* (2006.01)
*C07D 487/04* (2006.01)

(52) U.S. Cl.
CPC .......... *A61K 31/519* (2013.01); *C07D 487/04* (2013.01)

(58) Field of Classification Search
CPC .......................... C07D 487/04; A61K 31/519
See application file for complete search history.

(56) References Cited

U.S. PATENT DOCUMENTS

| | | | |
|---|---|---|---|
| 7,504,509 B2 | 3/2009 | Ibrahim et al. |
| 8,067,434 B2 | 11/2011 | Ibrahim et al. |
| 8,377,946 B1 | 2/2013 | Chen et al. |
| 8,673,928 B2 | 3/2014 | Ibrahim et al. |
| 8,940,893 B2 | 1/2015 | Bosanac et al. |
| 2005/0113395 A1 | 5/2005 | Changelian |
| 2007/0004675 A1 | 1/2007 | Saavedra et al. |
| 2007/0066641 A1 | 3/2007 | Ibrahim et al. |
| 2007/0135461 A1 | 6/2007 | Rodgers et al. |
| 2007/0275984 A1 | 11/2007 | Imoagi et al. |
| 2008/0161254 A1 | 7/2008 | Green et al. |
| 2009/0181959 A1 | 7/2009 | Rodgers et al. |
| 2009/0286782 A1 | 11/2009 | Ibrahim et al. |
| 2009/0286783 A1 | 11/2009 | Ibrahim et al. |
| 2010/0063047 A1 | 3/2010 | Borchardt et al. |
| 2011/0160203 A1 | 6/2011 | Liu et al. |
| 2013/0096136 A1 | 4/2013 | Hata et al. |
| 2015/0291593 A1 | 10/2015 | Su et al. |

FOREIGN PATENT DOCUMENTS

| | | |
|---|---|---|
| CN | 103664996 A | 3/2014 |
| JP | 2003321472 A | 11/2003 |
| WO | WO 93/20078 A1 | 10/1993 |
| WO | WO 98/07726 A1 | 2/1998 |
| WO | WO 02/50306 A1 | 6/2002 |
| WO | WO 02/051849 A1 | 7/2002 |
| WO | WO 2004/007479 A1 | 1/2004 |
| WO | WO 2004/056830 A1 | 7/2004 |
| WO | WO 2005/080377 A1 | 9/2005 |
| WO | WO 2005/117909 A2 | 12/2005 |
| WO | WO 2006/030031 A1 | 3/2006 |
| WO | WO 2006/032631 A1 | 3/2006 |
| WO | WO 2006/0421202 A2 | 4/2006 |
| WO | WO 2006/069080 A2 | 6/2006 |
| WO | WO 2007/013896 A2 | 2/2007 |

(Continued)

OTHER PUBLICATIONS

Dipaolo et al., "Specific Btk inhibition suppresses B cell- and myeloid cell-mediated arthritis", *Nature Chemical Biology* 2011, 7(1), p. 41-50.

Dorwald, "Side Reactions in Organic Synthesis: a guide to successful synthesis design", Weinheim:WILEY-VCH, 2005, Preface, 4 pages.

Hunter, "A Thousand and One Protein Kinases", *Cell*, Sep. 11, 1987, 50, p. 823-829.

(Continued)

*Primary Examiner* — Anna Pagonakis
(74) *Attorney, Agent, or Firm* — Dianne Pecoraro; John C. Todaro

(57) ABSTRACT

The application relates to a compound of Formula (I):

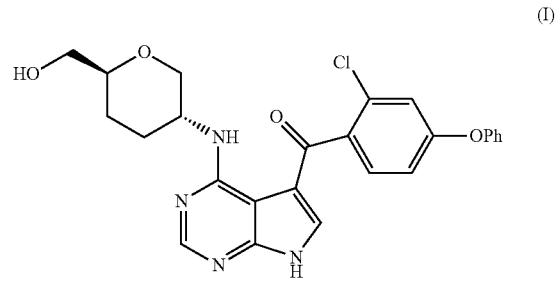

or a pharmaceutically acceptable salt thereof, tautomer, prodrug, solvate, metabolite, polymorph, analog or derivative thereof, which modulates the activity of BTK, a pharmaceutical composition comprising the compound of Formula (I), and a method of treating or preventing a disease in which BTK plays a role.

15 Claims, No Drawings

(56) References Cited

FOREIGN PATENT DOCUMENTS

| | | |
|---|---|---|
| WO | WO 2007/107545 A1 | 9/2007 |
| WO | WO 2007/125405 A2 | 11/2007 |
| WO | WO 2007/126841 A2 | 11/2007 |
| WO | WO 2008/006547 A2 | 1/2008 |
| WO | WO 2008/070908 A1 | 6/2008 |
| WO | WO 2008/075007 A1 | 6/2008 |
| WO | WO 2008/132155 A2 | 11/2008 |
| WO | WO 2008/135232 A1 | 11/2008 |
| WO | WO 2009/062118 A2 | 5/2009 |
| WO | WO 2009/134658 A2 | 11/2009 |
| WO | WO 2010/002954 A1 | 1/2010 |
| WO | WO 2010/039939 A1 | 4/2010 |
| WO | WO 2010/080996 A1 | 7/2010 |
| WO | WO 2011/044157 A1 | 4/2011 |
| WO | WO 2011/063159 A1 | 5/2011 |
| WO | WO 2011/082268 A2 | 7/2011 |
| WO | WO 2011/130628 A1 | 10/2011 |
| WO | WO 2011/133637 A2 | 10/2011 |
| WO | WO 2011/146882 A1 | 11/2011 |
| WO | WO 2011/149827 A1 | 12/2011 |
| WO | WO 2011/153553 A2 | 12/2011 |
| WO | WO 2012/027495 A1 | 3/2012 |
| WO | WO 2012/048058 A2 | 4/2012 |
| WO | WO 2012/109075 A1 | 8/2012 |
| WO | WO 2012/082275 A1 | 6/2013 |
| WO | WO 2013/082476 A1 | 6/2013 |
| WO | WO 2013/173506 A2 | 11/2013 |
| WO | WO 2013/182612 A1 | 12/2013 |
| WO | WO 2014/011911 A2 | 1/2014 |
| WO | WO 2014/015523 A1 | 1/2014 |
| WO | WO 2014/015675 A1 | 1/2014 |
| WO | WO 2014/015830 A1 | 1/2014 |
| WO | WO 2014/019908 A2 | 2/2014 |
| WO | WO 2014/039714 A2 | 3/2014 |
| WO | WO 2014/044691 A1 | 3/2014 |
| WO | WO 2014/047648 A1 | 3/2014 |
| WO | WO 2014/048869 A1 | 4/2014 |
| WO | WO 2014/048894 A1 | 4/2014 |
| WO | WO 2014/060432 A1 | 4/2014 |
| WO | WO 2014/144455 A1 | 9/2014 |
| WO | WO 2014/188173 A1 | 11/2014 |
| WO | WO 2014/194127 A1 | 12/2014 |
| WO | WO 2015/004024 A1 | 1/2015 |
| WO | WO 2015/083028 A1 | 6/2015 |
| WO | WO 2015/189620 A1 | 12/2015 |
| WO | WO 2016/044650 A1 | 3/2016 |
| WO | WO 2016/063080 A1 | 4/2016 |

OTHER PUBLICATIONS

Johnson et al. "Relationships between drug activity in NCI preclinical in vitro and in vivo models and early clinical trials", *British Journal of Cancer*, 2001, 84(10), p. 1424-1431.

Kriek, N. et al. "Synthesis of Novel Tetrahydropyran-Based Dipeptide Isosters by Overman Rearrangement of 2,3-Didehydroglycosides", *Eur. J. Org. Chem*. 2003, p. 2418-2427.

Liu et al. "Antiarthritis Effect of a Novel Bruton's Tyrosine Kinase (BTK) Inhibitor in Rat Collagen-Induced Arthritis and Mechanism-Based Pharmacokinetic/Pharmacodynamic Modeling: Relationships between Inhibition of BTK Phosphorylation and Efficacy", *The Journal of Pharmacology and Experimental Therapeutics*, 2011, 338(1), p. 154-163.

Sausville, "Contributions of human tumor xenografts to anticancer drug development", *Cancer Research*, 2006; 66(7), 2006.

Kim, A. "Clinical impact of gene expression profiling on oncology diagnosis, prognosis and treatment", Combinatorial Chemistry & High Throughput Screening, 2004, vol. 7, p. 183-206.

Alexeev V.V. "Optical Isomery and Pharmacological Activity of Drugs", St. Medical Academy, No. 1, 1998, p. 49-55. (English summary enclosed in the transmittal letter).

Bernstein J. "Polymorphism in Molecular Crystals" Polymorphism of Pharmaceuticals, 2007, ch. 7.3.2. Bioavailability, p. 324-330.

TETRAHYDROPYRANYL AMINO-PYRROLOPYRIMIDINONE AND METHODS OF USE THEREOF

RELATED APPLICATIONS

This application is a continuation of U.S. patent application Ser. No. 16/291,224, filed Mar. 4, 2019, which is a division of U.S. patent application Ser. No. 15/448,719, filed Mar. 3, 2017 (now U.S. Pat. No. 10,245,263), which is a continuation of U.S. patent application Ser. No. 14/757,745, filed Dec. 23, 2015 (now U.S. Pat. No. 9,630,968), the entire contents of each of which are incorporated herein by reference.

FIELD OF THE APPLICATION

The present application is directed to inhibitors of Bruton's Tyrosine Kinase (BTK), including mutant BTK, useful in the treatment of diseases or disorders associated with BTK kinase, including immune disorders, cancer, cardiovascular diseases, viral infections, inflammation, metabolism/endocrine function disorders, and neurological disorders. Specifically, the application is concerned with compounds and compositions thereof, which inhibit BTK, methods of treating diseases or disorders associated with BTK and methods of synthesis of these compounds.

BACKGROUND

BTK is a member of the Tec family of tyrosine kinases and plays an important role in the regulation of early B-cell development and mature B-cell activation and survival. (Hunter, Cell, 1987 50, 823-829). Functioning downstream of multiple receptors, such as growth factors, B-cell antigen, chemokine, and innate immune receptors, BTK initiates a number of cellular processes including cell proliferation, survival, differentiation, motility, angiogenesis, cytokine production, and antigen presentation.

BTK-deficient mouse models have shown the role BTK plays in allergic disorders and/or autoimmune disease and/or inflammatory disease. For instance, BTK deficiency in standard murine preclinical models of systemic lupus erythematosus (SLE) has been shown to result in a marked amelioration of disease progression. Furthermore, BTK-deficient mice can be resistant to developing collagen-induced arthritis and less susceptible to *Staphylococcus*-induced arthritis. Due to BTK's role in B-cell activation, BTK inhibitors can also be useful as inhibitors of B-cell mediated pathogenic activity (such as autoantibody production). Expression of BTK in osteoclasts, mast cells and monocytes has been shown to be important for the function of these cells. For example, impaired IgE-mediated mast cell activation and reduced TNF-alpha production by activated monocytes has been associated with BTK deficiency in mice and humans. Thus, BTK inhibition can be useful for the treatment of allergic disorders and/or autoimmune and/or inflammatory diseases such as: SLE, rheumatoid arthritis, multiple vasculitides, idiopathic thrombocytopenic purpura (ITP), myasthenia gravis, allergic rhinitis, and asthma (DiPaolo et. al., *Nature Chem. Biol.* 2011, 7(1):41-50; Liu et. al., *Jour. Pharmacol. and Exp. Ther.* 2011, 338(1):154-163).

Moreover, BTK's role in apoptosis demonstrates the utility of inhibition of BTK activity for the treatment of cancers, B-cell lymphoma, leukemia, and other hematological malignancies. In addition, given the role of BTK in osteoclast function, inhibition of BTK activity can be useful for the treatment of bone disorders such as osteoporosis.

Inhibition of BTK with small molecule inhibitors therefore has the potential to be a treatment for immune disorders, cancer, cardiovascular diseases, viral infections, inflammation, metabolism/endocrine function disorders, and neurological disorders. Thus, there remains a considerable need for potent small molecule inhibitors of BTK.

SUMMARY

A first aspect of the application relates to a compound of Formula (I):

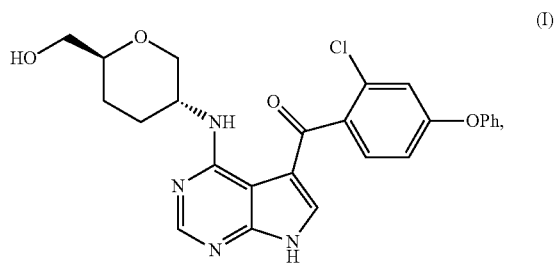 [SMILES: O=C(c1ccc(Oc2ccccc2)cc1Cl)c1c[nH]c2ncnc(N[C@@H]3CC[C@@H](CO)OC3)c12]

or pharmaceutically acceptable salts thereof, tautomers, prodrugs, solvates, metabolites, polymorphs, analogs or derivatives thereof. As used herein, the expressions "compound of Formula (I)" and "Compound (I)," refer to the same compound and can be used interchangeably.

Another aspect of the application relates to a pharmaceutical composition comprising the compound of Formula (I) or a pharmaceutically acceptable salt, tautomer, prodrug, solvate, metabolite, polymorph, analog or derivative thereof, and a pharmaceutically acceptable diluent, excipient or carrier.

Another aspect of the application relates to a method of treating a BTK-mediated disorder. The method comprises administering to a patient in need of a treatment for diseases or disorders associated with modulation of BTK kinase a therapeutically effective amount of the compound of Formula (I), or a pharmaceutically acceptable salt, tautomer, prodrug, solvate, metabolite, polymorph, analog or derivative thereof.

Another aspect of the application relates to a method of treating a BTK-mediated disorder. The method comprises administering to a patient in need of a treatment for diseases or disorders associated with modulation of BTK kinase a therapeutically effective amount of a pharmaceutical composition comprising the compound of Formula (I) or a pharmaceutically acceptable salt, tautomer, prodrug, solvate, metabolite, polymorph, analog or derivative thereof, and a pharmaceutically acceptable diluent, excipient or carrier.

Another aspect of the application relates to a method of treating a cell proliferative disorder. The method comprises administering to a patient in need thereof a therapeutically effective amount of the compound of Formula (I), or a pharmaceutically acceptable salt, tautomer, prodrug, solvate, metabolite, polymorph, analog or derivative thereof.

Another aspect of the application relates to a method of treating a cell proliferative disorder. The method comprises administering to a patient in need thereof a therapeutically effective amount of a pharmaceutical composition comprising the compound of Formula (I) or a pharmaceutically acceptable salt, tautomer, prodrug, solvate, metabolite, polymorph, analog or derivative thereof, and a pharmaceutically acceptable diluent, excipient or carrier.

Another aspect of the application relates to a method of treating cancer. The method comprises administering to a patient in need thereof a therapeutically effective amount of the compound of Formula (I), or a pharmaceutically acceptable salt, tautomer, prodrug, solvate, metabolite, polymorph, analog or derivative thereof.

Another aspect of the application relates to a method of treating cancer. The method comprises administering to a patient in need thereof a therapeutically effective amount of a pharmaceutical composition comprising the compound of Formula (I) or a pharmaceutically acceptable salt, tautomer, prodrug, solvate, metabolite, polymorph, analog or derivative thereof, and a pharmaceutically acceptable diluent, excipient or carrier.

Another aspect of the application relates to a method of modulating (e.g., inhibiting) BTK. The method comprises administering to a patient in need thereof a therapeutically effective amount of the compound of Formula (I), or a pharmaceutically acceptable salt, tautomer, prodrug, solvate, metabolite, polymorph, analog or derivative thereof.

Another aspect of the application relates to a method of modulating (e.g., inhibiting) BTK. The method comprises administering to a patient in need thereof a therapeutically effective amount of a pharmaceutical composition comprising the compound of Formula (I) or a pharmaceutically acceptable salt, tautomer, prodrug, solvate, metabolite, polymorph, analog or derivative thereof, and a pharmaceutically acceptable diluent, excipient or carrier.

Another aspect of the application relates to the compound of Formula (I) or a pharmaceutically acceptable salt, tautomer, prodrug, solvate, metabolite, polymorph, analog or derivative thereof, for use in a method of treating a BTK-mediated disorder, a cell proliferative disorder, or cancer, or of modulating (e.g., inhibiting) BTK. The compound of Formula (I), or a pharmaceutically acceptable salt, tautomer, prodrug, solvate, metabolite, polymorph, analog or derivative thereof is administered in a therapeutically effective amount to a patient in need thereof.

Another aspect of the application relates to a pharmaceutical composition comprising the compound of Formula (I) or a pharmaceutically acceptable salt, tautomer, prodrug, solvate, metabolite, polymorph, analog or derivative thereof, and a pharmaceutically acceptable diluent, excipient or carrier for use in a method of treating a BTK-mediated disorder, a cell proliferative disorder, or cancer, or of modulating (e.g., inhibiting) BTK. The composition is administered in a therapeutically effective amount to a patient in need thereof.

Another aspect of the application relates to the use of the compound of Formula (I) or a pharmaceutically acceptable salt, tautomer, prodrug, solvate, metabolite, polymorph, analog or derivative thereof, in the manufacture of a medicament for treating a BTK-mediated disorder, a cell proliferative disorder, or cancer, or for modulating (e.g., inhibiting) BTK. The compound of Formula (I), or a pharmaceutically acceptable salt, tautomer, prodrug, solvate, metabolite, polymorph, analog or derivative thereof is administered in a therapeutically effective amount to a patient in need thereof.

Another aspect of the application relates to the use of a pharmaceutical composition comprising the compound of Formula (I) or a pharmaceutically acceptable salt, tautomer, prodrug, solvate, metabolite, polymorph, analog or derivative thereof, and a pharmaceutically acceptable diluent, excipient or carrier in the manufacture of a medicament for treating a BTK-mediated disorder, a cell proliferative disorder, or cancer, or for modulating (e.g., inhibiting) BTK. The composition is administered in a therapeutically effective amount to a patient in need thereof The present application further provides methods of treating a disease or disorder associated with modulation of BTK kinase including, but not limited to, immune disorders, cancer, cardiovascular diseases, viral infections, inflammation, metabolism/endocrine function disorders, and neurological disorders comprising, administering to a patient suffering from at least one of said diseases or disorders the compound of Formula (I), or a pharmaceutically acceptable salt, tautomer, prodrug, solvate, metabolite, polymorph, analog or derivative thereof.

The present application provides inhibitors of BTK that are therapeutic agents in the treatment of diseases such as immune disorders, cancer, cardiovascular diseases, viral infections, inflammation, metabolism/endocrine function disorders, neurological disorders and other disease associated with the modulation of BTK kinase.

The present application further provides compounds and compositions with an improved efficacy and safety profile relative to known BTK inhibitors. The present application also provides agents with novel mechanisms of action toward BTK kinase in the treatment of various types of diseases including immune disorders, cancer, cardiovascular diseases, viral infections, inflammation, metabolism/endocrine function disorders, and neurological disorders. Ultimately the present application provides the medical community with a novel pharmacological strategy for the treatment of diseases and disorders associated with BTK kinase.

DETAILED DESCRIPTION

The present application relates to a compound and compositions that are capable of modulating the activity Bruton's Tyrosine Kinase (BTK). The application features methods of treating, preventing or ameliorating a disease or disorder in which BTK plays a role by administering to a patient in need thereof a therapeutically effective amount of the compound of Formula (I), or a pharmaceutically acceptable salt, tautomer, prodrug, solvate, metabolite, polymorph, analog or derivative thereof. The methods of the present application can be used in the treatment of a variety of BTK-mediated diseases and disorders by inhibiting the activity of BTK kinase. Inhibition of BTK provides treatment, prevention, or amelioration of diseases including, but not limited to, immune disorders, cancer, cardiovascular diseases, viral infections, inflammation, metabolism/endocrine function disorders and neurological disorders.

In a first aspect of the application, the compound of Formula (I) is described:

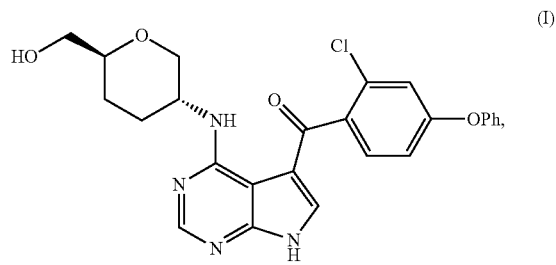 [SMILES: O=C(c1ccc(Oc2ccccc2)cc1Cl)c1c[nH]c2ncnc(N[C@@H]3CC[C@@H](CO)OC3)c12]

and pharmaceutically acceptable salts thereof, tautomers, prodrugs, solvates, metabolites, polymorphs, analogs or derivatives thereof.

In one embodiment, the compound of Formula (I) is a pharmaceutically acceptable salt. In another embodiment, the compound of Formula (I) is a hydrate. In yet another embodiment, the compound of Formula (I) is a solvate.

The details of the application are set forth in the accompanying description below. Although methods and materials similar or equivalent to those described herein can be used in the practice or testing of the present application, illustrative methods and materials are now described. Other features, objects, and advantages of the application will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this application belongs. All patents and publications cited in this specification are incorporated herein by reference in their entireties.

Definitions

The articles "a" and "an" are used in this application to refer to one or more than one (i.e., at least one) of the grammatical object of the article. By way of example, "an element" means one element or more than one element.

The term "and/or" is used in this application to mean either "and" or "or" unless indicated otherwise.

The application also includes pharmaceutical compositions comprising an effective amount of the compound of Formula (I) and a pharmaceutically acceptable carrier.

The term "carrier", as used in this application, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject.

The compound of Formula (I) may form salts which are also within the scope of this application. Reference to a compound of the Formula herein is understood to include reference to salts thereof, unless otherwise indicated.

Representative "pharmaceutically acceptable salts" include, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fumerate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

The compounds of the present application, for example, including the pharmaceutically acceptable salts, tautomers, prodrugs, and polymorphs of the compounds, can exist in a solvated form with other solvent molecules or in an unsolvated form.

"Solvate" means solvent addition forms that contain either stoichiometric or non stoichiometric amounts of solvent. Some compounds or salts have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this application, as are positional isomers (such as, for example, 4-pyridyl and 3-pyridyl). For example, if a compound of Formula (I) incorporates a double bond or a fused ring, both the cis- and trans-forms, as well as mixtures, are embraced within the scope of the application. Individual stereoisomers of the compound of the application may, for example, be substantially free of other isomers, or may be admixed, for example, as racemates or with all other, or other selected, stereoisomers. The chiral centers of the present application can have the S or R configuration as defined by the IUPAC 1974 Recommendations. The use of the terms "salt", "solvate", "ester," "prodrug" and the like, is intended to equally apply to the salt, solvate, ester and prodrug of enantiomers, stereoisomers, rotamers, tautomers, positional isomers, racemates or prodrugs of the inventive compounds.

The term "isomer" refers to compounds that have the same composition and molecular weight but differ in physical and/or chemical properties. The structural difference may be in constitution (geometric isomers) or in the ability to rotate the plane of polarized light (stereoisomers). With regard to stereoisomers, the compounds of Formula (I) may have one or more asymmetric carbon atom and may occur as racemates, racemic mixtures or as individual enantiomers or diastereomers.

In the present specification, the structural formula of the compound represents a certain isomer for convenience in some cases, but the present application includes all isomers, such as geometrical isomers, optical isomers based on an asymmetrical carbon, stereoisomers, tautomers, and the like.

"Isomerism" means compounds that have identical molecular formulae but differ in the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images of each other are termed "enantiomers" or sometimes optical isomers. A mixture containing equal amounts of individual enantiomeric forms of opposite chirality is termed a "racemic mixture".

The compounds of the application may contain asymmetric or chiral centers, and, therefore, exist in different stereoisomeric forms. It is intended that all stereoisomeric forms of the compounds of the application as well as mixtures thereof, including racemic mixtures, form part of the present application. In addition, the present application embraces all geometric and positional isomers. For example, if a compound of the application incorporates a double bond or a fused ring, both the cis- and trans-forms, as well as mixtures, are embraced within the scope of the application. Each compound herein disclosed includes all the enantiomers that conform to the general structure of the compound. The compound may be in a racemic or enantiomerically pure form, or any other form in terms of stereochemistry. The assay results may reflect the data collected for the racemic form, the enantiomerically pure form, or any other form in terms of stereochemistry.

A carbon atom bonded to four non-identical substituents is termed a "chiral center".

"Chiral isomer" means a compound with at least one chiral center. Compounds with more than one chiral center may exist either as an individual diastereomer or as a mixture of diastereomers, termed "diastereomeric mixture". When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

"Geometric isomer" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

In another embodiment of the application, the compound of Formula (I) is an enantiomer. In some embodiments the compound is the (S)-enantiomer. In other embodiments the compound is the (R)-enantiomer. In yet other embodiments, the compounds of Formula (I) may be (+) or (−) enantiomers. The compound may contain more than one stereocenter.

In another embodiment of the application, the compounds of Formula (I) are diastereomers. In some embodiments, the compounds are the syn diastereomer. In other embodiments, the compounds are the anti diastereomer.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Enantiomers can also be separated by use of a chiral HPLC column.

It is also possible that the compounds of the application may exist in different tautomeric forms, and all such forms are embraced within the scope of the application. Also, for example, all keto-enol and imine-enamine forms of the compounds are included in the application.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solid form, usually one tautomer predominates. In solutions where tautomerization is possible, a chemical equilibrium of the tautomers will be reached. The exact ratio of the tautomers depends on several factors, including temperature, solvent and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

Common tautomeric pairs are: ketone-enol, amide-nitrile, lactam-lactim, amide-imidic acid tautomerism in heterocyclic rings (e.g., in nucleobases such as guanine, thymine and cytosine), amine-enamine and enamine-imine. (Pyrrolopyrimidinyl)methanone-(Pyrrolopyrimidinyl)methanol tautomeric pairs are included in the present application:

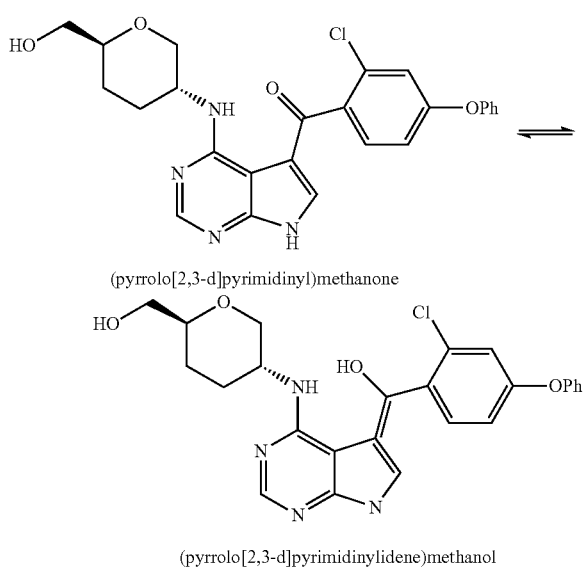

(pyrrolo[2,3-d]pyrimidinyl)methanone (pyrrolo[2,3-d]pyrimidinylidene)methanol

The present application relates to the compound of Formula (I) or pharmaceutically acceptable salts thereof, tautomers, prodrugs, solvates, metabolites, polymorphs, analogs or derivatives thereof, capable of inhibiting BTK, which are useful for the treatment of diseases and disorders associated with modulation of a BTK kinase. The application further relates to the compound of Formula (I), or pharmaceutically acceptable salts thereof, tautomers, prodrugs, solvates, metabolites, polymorphs, analogs or derivatives thereof, which are useful for inhibiting BTK. In some embodiments, the BTK is wild-type BTK. In other embodiments, the BTK is a mutant BTK.

Another aspect of the application relates to a compound of Formula (I), wherein the compound inhibits kinase activity of a mutant BTK, such as a drug-resistant mutant BTK harboring a drug-resistance mutation (e.g., C481S mutation). In some embodiments, the patient or subject does not respond to a BTK inhibitor or relapse after the treatment of a BTK inhibitor, due to a mutation of BTK kinase (e.g., a C481 S mutation) that prevents target inhibition. In one embodiment, the BTK mutation is a C481S mutation.

In some embodiments, the application provides a compound of Formula (I), wherein the compound is more potent than one or more known BTK inhibitors, including, but not limited to Ibrutinib, GDC-0834, RN486, CGI-560, CGI-1746, HM-71224, CC-292, ONO-4059, CNX-774, and LFM-A13, at inhibiting the activity of BTK. For example, the compound can be at least about 2-fold, 3-fold, 5-fold, 10-fold, 25-fold, 50-fold or about 100-fold more potent (e.g., as measured by $IC_{50}$) than Ibrutinib, GDC-0834, RN486, CGI-560, CGI-1746, HM-71224, CC-292, ONO-4059, CNX-774, and/or LFM-A13 at inhibiting the activity of the BTK.

In some embodiments, the application provides a compound of Formula (I), wherein the compound is more potent than one or more known BTK inhibitors, including, but not limited to Ibrutinib, GDC-0834, RN486, CGI-560, CGI-1746, HM-71224, CC-292, ONO-4059, CNX-774, and LFM-A13, at inhibiting the activity of BTK containing one or more mutations as described herein, e.g., C481S. For example, the compound can be at least about 2-fold, 3-fold, 5-fold, 10-fold, 25-fold, 50-fold or about 100-fold more potent (e.g., as measured by $IC_{50}$) than Ibrutinib, GDC-0834, RN486, CGI-560, CGI-1746, HM-71224, CC-292, ONO-4059, CNX-774, and/or LFM-A13 at inhibiting the activity of the BTK containing one or more mutations as described herein. A drug-resistant BTK mutant can have without limitation a drug resistance mutation comprising C481S mutation.

Potency of the inhibitor can be determined by $IC_{50}$ value. A compound with a lower $IC_{50}$ value, as determined under substantially similar conditions, is a more potent inhibitor relative to a compound with a higher $IC_{50}$ value.

The compounds of the present application can be converted to N-oxides by treatment with an oxidizing agent (e.g., 3-chloroperoxybenzoic acid (m-CPBA) and/or hydrogen peroxides) to afford other compounds of the present application. Thus, all shown and claimed nitrogen-containing compounds are considered, when allowed by valency and structure, to include both the compound as shown and its N-oxide derivative (which can be designated as N→O or $N^+$—$O^-$). Furthermore, in other instances, the nitrogens in the compounds of the present application can be converted to N-hydroxy or N-alkoxy compounds. For example, N-hydroxy compounds can be prepared by oxidation of the parent amine by an oxidizing agent such as m-CPBA. All shown and claimed nitrogen-containing compounds are also considered, when allowed by valency and structure, to cover both the compounds as shown and its N-hydroxy (i.e., N—OH) and N-alkoxy (i.e., N—OR, wherein R is substituted or unsubstituted $C_1$-$C_6$ alkyl, $C_1$-$C_6$ alkenyl, $C_1$-$C_6$ alkynyl, 3-14-membered carbocycle or 3-14-membered heterocycle) derivatives.

The term "prodrug," as used in this application, means a compound which is convertible in vivo by metabolic means (e.g., by hydrolysis) to a disclosed compound.

Since prodrugs are known to enhance numerous desirable qualities of pharmaceuticals (e.g., solubility, bioavailability, manufacturing, etc.) the compounds of Formula (I), or pharmaceutically acceptable salts, tautomers, solvates, metabolites, polymorphs, analogs or derivatives thereof can be delivered in prodrug form. Thus, the present application is intended to cover prodrugs of the compound of Formula (I), or a pharmaceutically acceptable salt, tautomer, solvate, metabolite, polymorph, analog or derivative thereof, methods of delivering the same and compositions containing the same. "Prodrugs" are intended to include any covalently bonded carriers that release an active parent drug of the present application in vivo when such prodrug is administered to a mammalian subject. Prodrugs are prepared by modifying functional groups present in the compound in such a way that the modifications are cleaved, either in routine manipulation or in vivo, to the parent compound. Prodrugs include compounds of the application wherein a hydroxyl or amino, group is bonded to any group that, when the prodrug of the present application is administered to a mammalian subject, it cleaves to form a free hydroxyl or free amino group, respectively. Examples of prodrugs include, but are not limited to, acetate, formate, and benzoate derivatives of alcohol and amine functional groups in the compounds of each of the formulae described herein or a pharmaceutically acceptable salt, tautomer, prodrug, solvate, metabolite, polymorph, analog or derivative thereof.

The term "crystal polymorphs", "polymorphs" or "crystal forms" means crystal structures in which a compound (or a salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

As used herein, the term "analog" refers to a compound that is structurally similar to another compound but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

The application also comprehends isotopically-labeled compounds, which are identical to those recited in the each of the formulae described herein, but for the fact that one or more atoms are replaced by an atom having an atomic mass or mass number different from the atomic mass or mass number most commonly found in nature. Examples of isotopes that can be incorporated into compounds of the application include isotopes of hydrogen, carbon, nitrogen, fluorine, such as $^3H$, $^{11}C$, $^{14}C$, $^2H$ and $^{18}F$.

The compound of Formula (I), or pharmaceutically acceptable salts, tautomers, prodrugs, solvates, metabolites, polymorphs, analogs or derivatives thereof, that contains the aforementioned isotopes and/or other isotopes of other atoms are within the scope of the present application. Isotopically-labeled compounds of the present application, for example those into which radioactive isotopes such as $^3H$, $^{14}C$ are incorporated, are useful in drug and/or substrate tissue distribution assays. Tritiated, i.e., $^3H$, and carbon-14, i.e., $^{14}C$, isotopes are useful for their ease of preparation and detectability. $^{11}C$ and $^{18}F$ isotopes are useful in PET (positron emission tomography). PET is useful in brain imaging. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances, isotopically labeled compounds of Formula (I), or pharmaceutically acceptable salts, tautomers, prodrugs, solvates, metabolites, polymorphs, analogs or derivatives thereof, can generally be prepared by carrying out the procedures disclosed in the Schemes and/or in the Examples described herein, by substituting a readily available isotopically labeled reagent for a non-isotopically labeled reagent. In one embodiment, the compound of Formula (I) or pharmaceutically acceptable salts, tautomers, prodrugs, solvates, metabolites, polymorphs, analogs or derivatives thereof, are not isotopically labelled.

The present application relates to a compound which is a modulator of BTK. In one embodiment, the compound of the present application is an inhibitor of BTK.

The term "administer", "administering", or "administration" as used in this application refers to either directly administering a disclosed compound or pharmaceutically acceptable salt of the disclosed compound or a composition to a subject, or administering a prodrug, derivative or analog of the compound or pharmaceutically acceptable salt of the compound or a composition to the subject, which can form an equivalent amount of active compound within the subject's body.

A "patient" or "subject" is a mammal, e.g., a human, mouse, rat, guinea pig, dog, cat, horse, cow, pig, or non-human primate, such as a monkey, chimpanzee, baboon or rhesus.

An "effective amount" or "therapeutically effective amount" when used in connection with a compound or pharmaceutical composition is an amount effective for treating or preventing a disease in a subject as described herein.

The term "treating" with regard to a subject, refers to improving at least one symptom of the subject's disorder. Treating includes curing, improving, or at least partially ameliorating the disorder.

The compounds of the present application, or a pharmaceutically acceptable salt, tautomer, prodrug, solvate, metabolite, polymorph, analog or derivative thereof, can also be used to prevent a disease, condition or disorder. As used herein, "preventing" or "prevent" describes reducing or eliminating the onset of the symptoms or complications of the disease, condition or disorder.

The term "disorder" is used in this application to mean, and is used interchangeably with, the terms disease, condition, or illness, unless otherwise indicated.

As used herein, the term "BTK-mediated" diseases or disorders means any disease or other deleterious condition in which BTK, or a mutant thereof, is known to play a role. Accordingly, another embodiment of the present application relates to treating or lessening the severity of one or more diseases in which BTK, or a mutant thereof, is known to play a role. Specifically, the present application relates to a method of treating or lessening the severity of a disease or condition selected from a proliferative disorder or an autoimmune disorder, wherein said method comprises administering to a patient in need thereof a compounds of Formula (I), or pharmaceutically acceptable salts, tautomers, prodrugs, solvates, metabolites, polymorphs, analogs or derivatives thereof, or a composition according to the present application.

As used herein, the term "cell proliferative disorder" refers to conditions in which unregulated or abnormal growth, or both, of cells can lead to the development of an unwanted condition or disease, which may or may not be cancerous. Exemplary cell proliferative disorders of the application encompass a variety of conditions wherein cell division is deregulated. Exemplary cell proliferative disorder include, but are not limited to, neoplasms, benign tumors, malignant tumors, pre-cancerous conditions, in situ tumors, encapsulated tumors, metastatic tumors, liquid tumors, solid tumors, immunological tumors, hematological tumors, cancers, carcinomas, leukemias, lymphomas, sarcomas, and rapidly dividing cells. The term "rapidly dividing cell" as used herein is defined as any cell that divides at a rate that exceeds or is greater than what is expected or observed among neighboring or juxtaposed cells within the same tissue. A cell proliferative disorder includes a precancer or a precancerous condition. A cell proliferative disorder includes cancer. Preferably, the methods provided herein are used to treat or alleviate a symptom of cancer. The term "cancer" includes solid tumors, as well as, hematologic tumors and/or malignancies. A "precancer cell" or "precancerous cell" is a cell manifesting a cell proliferative disorder that is a precancer or a precancerous condition. A "cancer cell" or "cancerous cell" is a cell manifesting a cell proliferative disorder that is a cancer. Any reproducible means of measurement may be used to identify cancer cells or precancerous cells. Cancer cells or precancerous cells can be identified by histological typing or grading of a tissue sample (e.g., a biopsy sample). Cancer cells or precancerous cells can be identified through the use of appropriate molecular markers.

Exemplary non-cancerous conditions or disorders include, but are not limited to, rheumatoid arthritis; inflammation; autoimmune disease; lymphoproliferative conditions; acromegaly; rheumatoid spondylitis; osteoarthritis; gout, other arthritic conditions; sepsis; septic shock; endotoxic shock; gram-negative sepsis; toxic shock syndrome; asthma; adult respiratory distress syndrome; chronic obstructive pulmonary disease; chronic pulmonary inflammation; inflammatory bowel disease; Crohn's disease; psoriasis; eczema; ulcerative colitis; pancreatic fibrosis; hepatic fibrosis; acute and chronic renal disease; irritable bowel syndrome; pyresis; restenosis; cerebral malaria; stroke and ischemic injury; neural trauma; Alzheimer's disease; Huntington's disease; Parkinson's disease; acute and chronic pain; allergic rhinitis; allergic conjunctivitis; chronic heart failure; acute coronary syndrome; cachexia; malaria; leprosy; leishmaniasis; Lyme disease; Reiter's syndrome; acute synovitis; muscle degeneration, bursitis; tendonitis; tenosynovitis; herniated, ruptures, or prolapsed intervertebral disk syndrome; osteopetrosis; thrombosis; restenosis; silicosis; pulmonary sarcosis; bone resorption diseases, such as osteoporosis; graft-versus-host reaction; Multiple Sclerosis; lupus; fibromyalgia; AIDS and other viral diseases such as Herpes Zoster, Herpes Simplex I or II, influenza virus and cytomegalovirus; and diabetes mellitus.

Exemplary cancers include, but are not limited to, adrenocortical carcinoma, AIDS-related cancers, AIDS-related lymphoma, anal cancer, anorectal cancer, cancer of the anal canal, appendix cancer, childhood cerebellar astrocytoma, childhood cerebral astrocytoma, basal cell carcinoma, skin cancer (non-melanoma), biliary cancer, extrahepatic bile duct cancer, intrahepatic bile duct cancer, bladder cancer, urinary bladder cancer, bone and joint cancer, osteosarcoma and malignant fibrous histiocytoma, brain cancer, brain tumor, brain stem glioma, cerebellar astrocytoma, cerebral astrocytoma/malignant glioma, ependymoma, medulloblastoma, supratentorial primitive neuroectodermal tumors, visual pathway and hypothalamic glioma, breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Seziary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin lymphoma, hypopharyngeal cancer, intraocular melanoma, ocular cancer, islet cell tumors (endocrine pancreas), Kaposi Sarcoma, kidney cancer, renal cancer, kidney cancer, laryngeal cancer, acute lymphoblastic leukemia, acute myeloid leukemia, chronic lymphocytic leukemia, chronic myelogenous leukemia, hairy cell leukemia, lip and oral cavity cancer, liver cancer, lung cancer, non-small cell lung cancer, small cell lung cancer, AIDS-related lymphoma, non-Hodgkin lymphoma, primary central nervous system lymphoma, Waldenstram macroglobulinemia, medulloblastoma, melanoma, intraocular (eye) melanoma, merkel cell carcinoma, mesothelioma malignant, mesothelioma, metastatic squamous neck cancer, mouth cancer, cancer of the tongue, multiple endocrine neoplasia syndrome, mycosis fungoides, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, ewing family of sarcoma tumors, Kaposi Sarcoma, soft tissue sarcoma, uterine cancer, uterine sarcoma, skin cancer (non-melanoma), skin cancer (melanoma), merkel cell skin carcinoma, small intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, endometrial uterine cancer, uterine sarcoma, uterine corpus cancer, vaginal cancer, vulvar cancer, and Wilm's Tumor.

Method for Preparing the Compounds

The compounds of the present application may be made by a variety of methods, including standard chemistry. A suitable synthetic route is depicted in the Schemes given below.

The compound of Formula (I) may be prepared by methods known in the art of organic synthesis as set forth in part by the following synthetic schemes. In the scheme described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of the compounds of the present application.

Those skilled in the art will recognize if a stereocenter exists in the compound of Formula (I). Accordingly, the present application includes both possible stereoisomers (unless specified in the synthesis) and includes not only racemic compound but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

The compounds described herein may be made from commercially available starting materials or synthesized using known organic, inorganic, and/or enzymatic processes.

The compounds of the present application can be prepared in a number of ways well known to those skilled in the art of organic synthesis. By way of example, the compounds of the present application can be synthesized using the methods described below, together with synthetic methods known in the art of synthetic organic chemistry, or variations thereon as appreciated by those skilled in the art. Preferred methods include but are not limited to those methods described below. The compounds of the present application (i.e., the compound of Formula (I)) can be synthesized by following the steps outlined in General Scheme 1 which comprises a sequence of assembling intermediates 2-a to 2-h. Starting materials are either commercially available or made by known procedures in the reported literature or as illustrated.

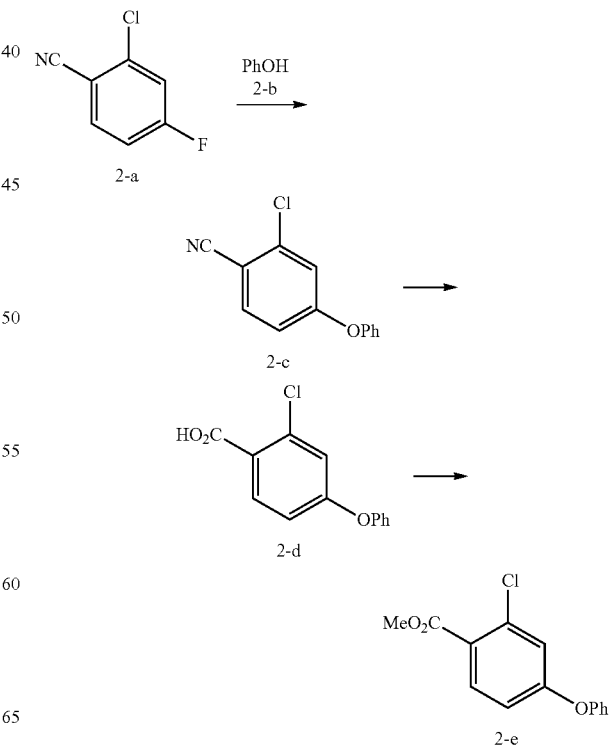

General Scheme 1

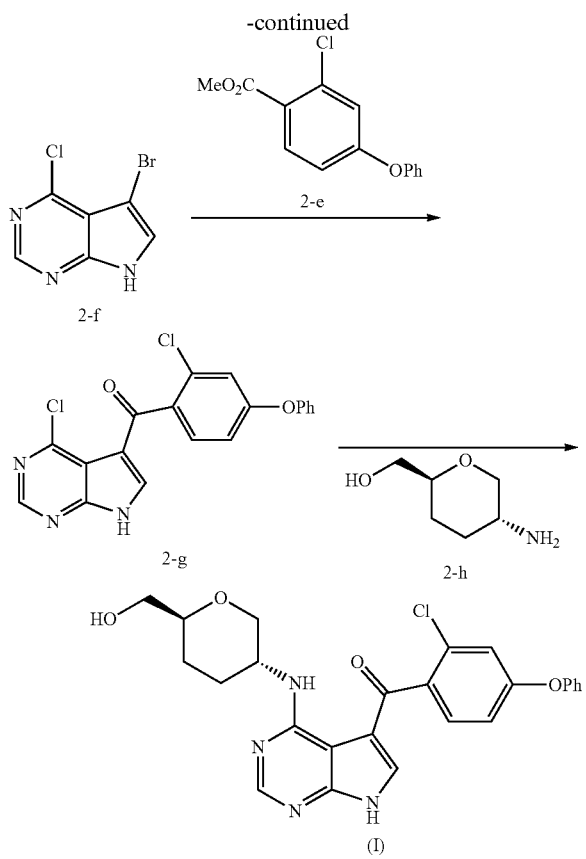

The general way of preparing the compound of Formula (I) by using intermediates 2-a, 2-b, 2-c, 2-d, 2-e, 2-f, 2-g, and 2-h is outlined in General Scheme 1. Nucleophilic addition of phenol 2-b to 2-chloro-4-fluorobenzonitrile 2-a using a strong base, e.g., sodium hydride (NaH), in a solvent, e.g., N,N-dimethylformamide (DMF), yields 2-c. Hydrolysis of 2-c using a base, e.g., potassium hydroxide (KOH), in a solvent, e.g., ethanol, at an elevated temperature yields carboxylic acid 2-d. Esterification of 2-d with methyl iodide using a base, e.g., potassium carbonate ($K_2CO_3$) or cesium carbonate ($Cs_2CO_3$), in a solvent, e.g., N,N-dimethylformamide (DMF), provides 2-e. Acylation of intermediate 2-f with 2-e using a strong base, e.g., n-butyl lithium (n-BuLi), in a solvent, e.g., tetrahydrofuran (THF), provides 2-g. Nucleophilic addition of amine 2-h to aryl chloride 2-g using a base, e.g., N,N-diisopropylethylamine (DIPEA), and optionally in a solvent, e.g., N,N-dimethylformamide (DMF), provides the compound of Formula (I).

A mixture of enantiomers, diastereomers, cis/trans isomers resulting from the process described above can be separated into their single components by chiral salt technique, chromatography using normal phase, reverse phase or chiral column, depending on the nature of the separation.

Biological Assays
BTK Kinase Activity Assay

Test inhibitor and controls are prepared in a solvent (i.e., DMSO), and added to each well of a reaction plate. Full-length active BTK is diluted in assay buffer and added to each well. After pre-incubation, the kinase reaction is initiated by the addition of an activation mixture diluted in assay buffer containing biotinylated PLCγ2 peptide and ATP. The plates are incubated and the reactions are then stopped in the dark by the addition of stop/detection mixture prepared in assay buffer. Assay plates are incubated in the dark, and the plates are read on a plate reader.

BTK C481S Kinase Activity Assay

Test inhibitors and controls are prepared in a solvent (i.e., DMSO) at the desired final concentration, and added to each well of a reaction plate. Full-length BTKC481S is diluted in assay buffer and added to each well in a volume. After pre-incubation, the kinase reaction is initiated by the addition of an activation mixture diluted in assay buffer containing biotinylated PLCγ2 peptide, and ATP. The plates are incubated and the reactions are then stopped in the dark by the addition of a stop/detection mixture prepared in assay buffer. Assay plates are incubated in the dark, and the plates are read on a plate reader.

Anti-Proliferation Assay

Cell survival is determined by a MTS assay. Briefly, cells (i.e., TMD-8 cells or Rec-1 cells) are plated in a 96-well plate, cultured in complete growth medium, and then treated with various drugs and drug combinations. MTS/PMS is added and incubated, followed by assessment of cell viability using the microplate reader. Data is normalized to untreated controls and analyzed with Microsoft Excel.

Methods of Using the Compounds

Another aspect of the application relates to a method of treating, preventing, inhibiting, or eliminating a disease or disorder associated with modulation of BTK (e.g., inhibition of BTK). The method comprises administering to a patient in need of a treatment for diseases or disorders associated with modulation of BTK an effective amount the compound of Formula (I), or a pharmaceutically acceptable salt, tautomer, prodrug, solvate, metabolite, polymorph, analog or derivative thereof or a pharmaceutical composition of the compound of Formula (I). In one embodiment, the BTK-mediated disorder is selected from immune disorders, cancer, cardiovascular diseases, viral infections, inflammation, metabolism/endocrine function disorders and neurological disorders. In some embodiments, the method further comprises administering an additional therapeutic agent selected from an anti-inflammatory agent, an immunomodulatory agent, chemotherapeutic agent, a neurotropic factor, an agent for treating cardiovascular disease, an agent for treating liver disease, an anti-viral agent, an agent for treating blood disorders, an agent for treating diabetes, and an agent for treating immunodeficiency disorders. In some embodiments, the BTK is wild-type BTK. In other embodiments, the BTK is mutant BTK (e.g., BTK C481S mutant).

Another aspect of the application relates to a method of treating, preventing, inhibiting, or eliminating a cell proliferative disorder, the method comprising administering to a patient in need thereof a therapeutically effective amount of the compound of Formula (I), or a pharmaceutically acceptable salt, tautomer, prodrug, solvate, metabolite, polymorph, analog or derivative thereof or a pharmaceutical composition of the compound of Formula (I). In one embodiment, the cell proliferative disorder is a cancer. In some embodiments, the method further comprises administering an additional therapeutic agent selected from an anti-inflammatory agent, an immunomodulatory agent, chemotherapeutic agent, a neurotropic factor, an agent for treating cardiovascular disease, an agent for treating liver disease, an anti-viral agent, an agent for treating blood disorders, an agent for treating diabetes, and an agent for treating immunodeficiency disorders.

Another aspect of the application relates to a method of modulating BTK, the method comprising administering to a patient in need thereof a therapeutically effective amount of the compound of Formula (I), or a pharmaceutically acceptable salt, tautomer, prodrug, solvate, metabolite, polymorph, analog or derivative thereof or a pharmaceutical composition of the compound of Formula (I). In one embodiment, modulating BTK is inhibiting BTK. In some embodiments, the BTK is wild-type BTK. In other embodiments, the BTK is mutant BTK (e.g., BTK C481S mutant).

Another aspect of the application relates to the compound of Formula (I), or a pharmaceutically acceptable salt, tautomer, prodrug, solvate, metabolite, polymorph, analog or derivative thereof, for use in a method of treating a BTK-mediated disorder. In one embodiment, the disease or disorder is selected from immune disorders, cancer, cardiovascular diseases, viral infections, inflammation, metabolism/endocrine function disorders and neurological disorders. In some embodiments, the method further comprises administering an additional therapeutic agent selected from an anti-inflammatory agent, an immunomodulatory agent, chemotherapeutic agent, a neurotropic factor, an agent for treating cardiovascular disease, an agent for treating liver disease, an anti-viral agent, an agent for treating blood disorders, an agent for treating diabetes, and an agent for treating immunodeficiency disorders. In some embodiments, the BTK is wild-type BTK. In other embodiments, the BTK is mutant BTK (e.g., BTK C481S mutant).

In another aspect, the present application relates to a pharmaceutical composition of the compound of Formula (I), or a pharmaceutically acceptable salt, tautomer, prodrug, solvate, metabolite, polymorph, analog or derivative thereof, for use in a method of treating a BTK-mediated disorder. In one embodiment, the disease or disorder is selected from immune disorders, cancer, cardiovascular diseases, viral infections, inflammation, metabolism/endocrine function disorders and neurological disorders. In some embodiments, the method further comprises administering an additional therapeutic agent selected from an anti-inflammatory agent, an immunomodulatory agent, chemotherapeutic agent, a neurotropic factor, an agent for treating cardiovascular disease, an agent for treating liver disease, an anti-viral agent, an agent for treating blood disorders, an agent for treating diabetes, and an agent for treating immunodeficiency disorders. In some embodiments, the BTK is wild-type BTK. In other embodiments, the BTK is mutant BTK (e.g., BTK C481S mutant).

Another aspect of the application relates to the compound of Formula (I), or a pharmaceutically acceptable salt, tautomer, prodrug, solvate, metabolite, polymorph, analog or derivative thereof, for use in a method of treating, preventing, inhibiting, or eliminating a cell proliferative disorder. In one embodiment, the cell proliferative disorder is a cancer.

In another aspect, the present application relates to a pharmaceutical composition of the compound of Formula (I), or a pharmaceutically acceptable salt, tautomer, prodrug, solvate, metabolite, polymorph, analog or derivative thereof, for use in a method of treating, preventing, inhibiting, or eliminating a cell proliferative disorder. In one embodiment, the cell proliferative disorder is a cancer.

Another aspect of the application relates to the compound of Formula (I), or a pharmaceutically acceptable salt, tautomer, prodrug, solvate, metabolite, polymorph, analog or derivative thereof, for use in modulating BTK. In one embodiment, modulating BTK is inhibiting BTK. In some embodiments, the BTK is wild-type BTK. In other embodiments, the BTK is mutant BTK (e.g., BTK C481S mutant).

In another aspect, the present application relates to a pharmaceutical composition of the compound of Formula (I), or a pharmaceutically acceptable salt, tautomer, prodrug, solvate, metabolite, polymorph, analog or derivative thereof, for use in modulating BTK. In one embodiment, modulating BTK is inhibiting BTK. In some embodiments, the BTK is wild-type BTK. In other embodiments, the BTK is mutant BTK (e.g., BTK C481S mutant).

Another aspect of the application relates to the use of the compound of Formula (I), or a pharmaceutically acceptable salt, tautomer, prodrug, solvate, metabolite, polymorph, analog or derivative thereof, in the manufacture of a medicament for treating a BTK-mediated disease or disorder. In one embodiment, the disease or disorder is selected from immune disorders, cancer, cardiovascular diseases, viral infections, inflammation, metabolism/endocrine function disorders and neurological disorders. In some embodiments, the treatment further comprises administering an additional therapeutic agent selected from an anti-inflammatory agent, an immunomodulatory agent, chemotherapeutic agent, a neurotropic factor, an agent for treating cardiovascular disease, an agent for treating liver disease, an anti-viral agent, an agent for treating blood disorders, an agent for treating diabetes, and an agent for treating immunodeficiency disorders. In some embodiments, the BTK is wild-type BTK. In other embodiments, the BTK is mutant BTK (e.g., BTK C481S mutant).

In another aspect, the present application relates to the use of a pharmaceutical composition of the compound of Formula (I), or a pharmaceutically acceptable salt, tautomer, prodrug, solvate, metabolite, polymorph, analog or derivative thereof, in the manufacture of a medicament for treating a BTK-mediated disease or disorder. In one embodiment, the disease or disorder is selected from immune disorders, cancer, cardiovascular diseases, viral infections inflammation, metabolism/endocrine function disorders and neurological disorders. In some embodiments, the treatment further comprises administering an additional therapeutic agent selected from an anti-inflammatory agent, an immunomodulatory agent, chemotherapeutic agent, a neurotropic factor, an agent for treating cardiovascular disease, an agent for treating liver disease, an anti-viral agent, an agent for treating blood disorders, an agent for treating diabetes, and an agent for treating immunodeficiency disorders. In some embodiments, the BTK is wild-type BTK. In other embodiments, the BTK is mutant BTK (e.g., BTK C481S mutant).

Another aspect of the application relates to the use of the compound of Formula (I), or a pharmaceutically acceptable salt, tautomer, prodrug, solvate, metabolite, polymorph, analog or derivative thereof, in the manufacture of a medicament for treating, preventing, inhibiting, or eliminating a cell proliferative disorder. In one embodiment, the cell proliferative disorder is a cancer.

In another aspect, the present application relates to the use of a pharmaceutical composition of the compound of Formula (I), or a pharmaceutically acceptable salt, tautomer, prodrug, solvate, metabolite, polymorph, analog or derivative thereof, in the manufacture of a medicament for treating, preventing, inhibiting, or eliminating a cell proliferative disorder. In one embodiment, the cell proliferative disorder is a cancer.

Another aspect of the application relates to the use of the compound of Formula (I), or a pharmaceutically acceptable salt, tautomer, prodrug, solvate, metabolite, polymorph, analog or derivative thereof, in the manufacture of a medicament for modulating BTK. In one embodiment, modulating BTK is inhibiting BTK. In some embodiments, the BTK is wild-type BTK. In other embodiments, the BTK is mutant BTK (e.g., BTK C481S mutant).

In another aspect, the present application relates to the use of a pharmaceutical composition of the compound of Formula (I), or a pharmaceutically acceptable salt, tautomer, prodrug, solvate, metabolite, polymorph, analog or derivative thereof, in the manufacture of a medicament for modulating BTK. In one embodiment, modulating BTK is inhibiting BTK. In some embodiments, the BTK is wild-type BTK. In other embodiments, the BTK is mutant BTK (e.g., BTK C481S mutant).

In some embodiments of the methods and uses described herein, the cancer is selected from breast, ovary, cervix, prostate, testis, genitourinary tract, esophagus, larynx, glioblastoma, neuroblastoma, stomach, skin, keratoacanthoma, lung, epidermoid carcinoma, large cell carcinoma, non-small cell lung carcinoma (NSCLC), small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, pancreatic, myeloid disorders, lymphoma, hairy cells, buccal cavity, naso-pharyngeal, pharynx, lip, tongue, mouth, small intestine, colon-rectum, large intestine, rectum, brain and central nervous system, Hodgkin's leukemia, bronchus, thyroid, liver and intrahepatic bile duct, hepatocellular, gastric, glioma/glioblastoma, endometrial, melanoma, kidney and renal pelvis, urinary bladder, uterine corpus, uterine cervix, multiple myeloma, acute myelogenous leukemia, chronic myelogenous leukemia, lymphocytic leukemia, chronic lymphoid leukemia (CLL), myeloid leukemia, oral cavity and pharynx, non-Hodgkin lymphoma, melanoma, and villous colon adenoma.

In any of the embodiments of the application, the cancer can be any cancer in any organ, for example, a cancer is selected from the group consisting of glioma, thyroid carcinoma, breast carcinoma, small-cell lung carcinoma, non-small-cell carcinoma, gastric carcinoma, colon carcinoma, gastrointestinal stromal carcinoma, pancreatic carcinoma, bile duct carcinoma, CNS carcinoma, ovarian carcinoma, endometrial carcinoma, prostate carcinoma, renal carcinoma, anaplastic large-cell lymphoma, leukemia, multiple myeloma, mesothelioma, and melanoma, and combinations thereof.

In some embodiments of the methods and uses described herein, the disease or disorder is an immune disorder. In one embodiment, the immune disorder is rheumatoid arthritis.

In some embodiments of the methods and uses described herein, the disease or disorder is systemic and local inflammation, arthritis, inflammation related to immune suppression, organ transplant rejection, allergies, ulcerative colitis, Crohn's disease, dermatitis, asthma, systemic lupus erythematosus, Sjogren's Syndrome, multiple sclerosis, scleroderma/systemic sclerosis, idiopathic thrombocytopenic purpura (ITP), anti-neutrophil cytoplasmic antibodies (ANCA) vasculitis, chronic obstructive pulmonary disease (COPD), psoriasis.

In one embodiment, methods of treating a disease or disorder associated with modulation of BTK including, immune disorders, cancer, cardiovascular diseases, viral infections, inflammation, metabolism/endocrine function disorders and neurological disorders, comprise administering to a patient suffering from at least one of said diseases or disorder the compound of Formula (I).

The disclosed compound of the application can be administered in effective amounts to treat or prevent a disorder and/or prevent the development thereof in subjects.

The compound of the application can be administered in therapeutically effective amounts in a combinational therapy with one or more therapeutic agents (pharmaceutical combinations) or modalities, e.g., non-drug therapies. For example, synergistic effects can occur with other antiproliferative, anti-cancer, immunomodulatory or anti-inflammatory substances. In some embodiments, the compound of Formula (I) is administered in combination with an additional therapeutic agent selected from an anti-inflammatory agent, an immunomodulatory agent, chemotherapeutic agent, a neurotropic factor, an agent for treating cardiovascular disease, an agent for treating liver disease, an anti-viral agent, an agent for treating blood disorders, an agent for treating diabetes, and an agent for treating immunodeficiency disorders. Where the compound of the application is administered in conjunction with other therapies, dosages of the co-administered compounds will of course vary depending on the type of co-drug employed, on the specific drug employed, on the condition being treated and so forth.

Combination therapy includes the administration of the subject compound in further combination with other biologically active ingredients (such as, but not limited to, an anti-inflammatory agent, an immunomodulatory agent, chemotherapeutic agent, a neurotropic factor, an agent for treating cardiovascular disease, an agent for treating liver disease, an anti-viral agent, an agent for treating blood disorders, an agent for treating diabetes, and an agent for treating immunodeficiency disorders) and non-drug therapies (such as, but not limited to, surgery or radiation treatment). For instance, the compound of the application can be used in combination with other pharmaceutically active compounds, preferably compounds that are able to enhance the effect of the compound of the application. The compound of the application can be administered simultaneously (as a single preparation or separate preparation) or sequentially to the other drug therapy or treatment modality. In general, a combination therapy envisions administration of two or more drugs during a single cycle or course of therapy.

Pharmaceutical Compositions

The present application also provides pharmaceutical compositions comprising the compound of Formula (I), or a pharmaceutically acceptable salt, tautomer, prodrug, solvate, metabolite, polymorph, analog or derivative thereof, in combination with at least one pharmaceutically acceptable excipient or carrier.

A "pharmaceutical composition" is a formulation containing the compound of the present application in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed compound or a pharmaceutically acceptable salt, tautomer, prodrug, solvate, metabolite, polymorph, analog or derivative thereof thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this application include powders, sprays, ointments, pastes, creams, lotions, gels, solutions, patches and inhalants. In one embodiment, the active compound is mixed under sterile conditions with a pharmaceutically acceptable carrier, and with any preservatives, buffers or propellants that are required.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

A pharmaceutical compositions of the application are formulated to be compatible with its intended route of administration. Examples of routes of administration include parenteral, e.g., intravenous, intradermal, subcutaneous, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A compound or pharmaceutical composition of the application can be administered to a subject in many of the well-known methods currently used for chemotherapeutic treatment. For example, for treatment of cancers, a compound of the application may be injected directly into tumors, injected into the blood stream or body cavities or taken orally or applied through the skin with patches. The dose chosen should be sufficient to constitute effective treatment but not as high as to cause unacceptable side effects. The state of the disease condition (e.g., cancer, precancer, and the like) and the health of the patient should preferably be closely monitored during and for a reasonable period after treatment.

The term "therapeutically effective amount", as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician. In one embodiment, the disease or disorder is selected from immune disorders, cancer, cardiovascular diseases, viral infections, inflammation, metabolism/endocrine function disorders and neurological disorders. In another embodiment, the disease or condition to be treated is cancer. In another embodiment, the disease or condition to be treated is a cell proliferative disorder.

For any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing active compound (i.e., the compound of Formula (I)) of the present application may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compound into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compound is delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compound is formulated into ointments, salves, gels, or creams as generally known in the art.

The active compound can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the application are dictated by and directly dependent on the unique characteristics of the active compound and the particular therapeutic effect to be achieved.

In therapeutic applications, the dosages of the pharmaceutical compositions used in accordance with the application vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the growth of the tumors and also preferably causing complete regression of the cancer. Dosages can range from about 0.01 mg/kg per day to about 5000 mg/kg per day. An effective amount of a pharmaceutical agent is that which provides an objectively identifiable improvement as noted by the clinician or other qualified observer. For example, regression of a tumor in a patient may be measured with reference to the diameter of a tumor. Decrease in the diameter of a tumor indicates regression. Regression is also indicated by failure of tumors to reoccur after treatment has stopped. As used herein, the term "dosage effective manner" refers to amount of an active compound to produce the desired biological effect in a subject or cell.

The pharmaceutical compositions can be included in a container, pack, or dispenser together with instructions for administration.

As used herein, "pharmaceutically acceptable salts" refer to derivatives of the compound of the present application wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present application also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

It should be understood that all references to pharmaceutically acceptable salts include solvent addition forms (solvates) or crystal forms (polymorphs) as defined herein, of the same salt.

The compound of the present application can also be prepared as esters, for example, pharmaceutically acceptable esters. For example, a carboxylic acid function group in a compound can be converted to its corresponding ester, e.g., a methyl, ethyl or other ester. Also, an alcohol group in a compound can be converted to its corresponding ester, e.g., an acetate, propionate or other ester.

The compound of the present application can also be prepared as prodrugs, for example, pharmaceutically acceptable prodrugs. The terms "pro-drug" and "prodrug" are used interchangeably herein and refer to any compound which releases an active parent drug in vivo. Since prodrugs are known to enhance numerous desirable qualities of pharmaceuticals (e.g., solubility, bioavailability, manufacturing, etc.), the compound of the present application can be delivered in prodrug form. Thus, the present application is intended to cover prodrugs of the presently claimed compound, methods of delivering the same and compositions containing the same. "Prodrugs" are intended to include any covalently bonded carriers that release an active parent drug of the present application in vivo when such prodrug is administered to a subject. Prodrugs in the present application are prepared by modifying functional groups present in the compound in such a way that the modifications are cleaved, either in routine manipulation or in vivo, to the parent compound. Prodrugs include the compound of the present application wherein a hydroxy, amino, sulfhydryl, carboxy or carbonyl group is bonded to any group that may be cleaved in vivo to form a free hydroxyl, free amino, free sulfhydryl, free carboxy or free carbonyl group, respectively.

Examples of prodrugs include, but are not limited to, esters (e.g., acetate, dialkylaminoacetates, formates, phosphates, sulfates and benzoate derivatives) and carbamates (e.g., N,N-dimethylaminocarbonyl) of hydroxy functional groups, esters (e.g., ethyl esters, morpholinoethanol esters) of carboxyl functional groups, N-acyl derivatives (e.g., N-acetyl) N-Mannich bases, Schiff bases and enaminones of amino functional groups, oximes, acetals, ketals and enol esters of ketone and aldehyde functional groups in the compound of the application, and the like, See Bundegaard, H., *Design of Prodrugs*, p 1-92, Elsevier, New York-Oxford (1985).

The compound, or pharmaceutically acceptable salts, tautomers, prodrugs, solvates, metabolites, polymorphs, analogs or derivatives thereof, are administered orally, nasally, transdermally, pulmonary, inhalationally, buccally, sublingually, intraperintoneally, subcutaneously, intramuscularly, intravenously, rectally, intrapleurally, intrathecally and parenterally. In one embodiment, the compound or a pharmaceutically acceptable salt, tautomer, prodrug, solvate, metabolite, polymorph, analog or derivative thereof is administered orally. One skilled in the art will recognize the advantages of certain routes of administration.

The dosage regimen utilizing the compound is selected in accordance with a variety of factors including type, species, age, weight, sex and medical condition of the patient; the severity of the condition to be treated; the route of administration; the renal and hepatic function of the patient; and the particular compound or pharmaceutically acceptable salt, tautomer, prodrug, solvate, metabolite, polymorph, analog or derivative thereof employed. An ordinarily skilled physician or veterinarian can readily determine and prescribe the effective amount of the drug required to prevent, counter or arrest the progress of the condition.

Techniques for formulation and administration of the disclosed compound of the application can be found in *Remington: the Science and Practice of Pharmacy*, 19$^{th}$ edition, Mack Publishing Co., Easton, Pa. (1995). In an embodiment, the compound described herein, and the pharmaceutically acceptable salts, tautomers, prodrugs, solvates, metabolites, polymorphs, analogs or derivatives thereof, are used in pharmaceutical preparations in combination with a pharmaceutically acceptable carrier or diluent. Suitable pharmaceutically acceptable carriers include inert solid fillers or diluents and sterile aqueous or organic solutions. The compound or pharmaceutically acceptable salts, prodrugs, solvates, metabolites, polymorphs, analogs or derivatives thereof will be present in such pharmaceutical compositions in amounts sufficient to provide the desired dosage amount in the range described herein.

All percentages and ratios used herein, unless otherwise indicated, are by weight. Other features and advantages of the present application are apparent from the different examples. The provided examples illustrate different components and methodology useful in practicing the present application. The examples do not limit the claimed application. Based on the present application the skilled artisan can identify and employ other components and methodology useful for practicing the present application.

EXAMPLES

The application is further illustrated by the following examples and synthesis schemes, which are not to be construed as limiting this application in scope or spirit to the specific procedures herein described. It is to be understood that the examples are provided to illustrate certain embodiments and that no limitation to the scope of the application is intended thereby. It is to be further understood that resort may be had to various other embodiments, modifications, and equivalents thereof which may suggest themselves to those skilled in the art without departing from the spirit of the present application and/or scope of the appended claims.
Analytical Methods, Materials, and Instrumentation Unless otherwise noted, reagents and solvents were used as received from commercial suppliers. Proton nuclear magnetic resonance (NMR) spectra were obtained on either Bruker or Varian spectrometers at 400 MHz. Spectra are given in ppm (δ) and coupling constants, J, are reported in Hertz. Tetramethylsilane (TMS) was used as an internal standard. Mass spectra were collected using a Waters ZQ Single Quad Mass Spectrometer (ion trap ESI). Purity and low resolution mass spectral data were measured using Waters Acquity i-class ultra-performance liquid chromatography (UPLC) system with Acquity Photo Diode Array Detector, Acquity Evaporative Light Scattering Detector (ELSD) and Waters ZQ Mass Spectrometer. Data was acquired using Waters MassLynx 4.1 software and purity characterized by UV wavelength 220 nm, ELSD and ESI. Column: Acquity UPLC BEH C18 1.7 μm 2.1×50 mm; Flow rate 0.6 mL/min; Solvent A (95/5/0.1 10 mM ammonium formate/acetonitrile/formic acid), Solvent B (95/5/0.09 acetonitrile/water/formic acid); gradient: 5-100% B from 0 to 2 min, hold 100% B to 2.2 min, then 5% B at 2.21 min. Abbreviations used in the following examples and elsewhere herein are:

DCM dichloromethane
DIEA N,N-diisopropylethylamine
DIPEA N,N-diisopropylethylamine
DMF N,N-dimethylformamide
DMSO dimethylsulfoxide
DTT Dithiothreitol
EDTA ethylenediaminetetraacetic acid
EGTA ethylene glycol tetraacetic acid
Et$_2$O diethyl ether
EtOAc ethyl acetate
EtOH ethanol
LCMS liquid chromatography-mass spectrometry
MeOH methanol
MS mass spectrometry
NMR nuclear magnetic resonance
ppm parts per million Example 1: 2-chloro-4-phenoxybenzoate (Intermediate 2-D)

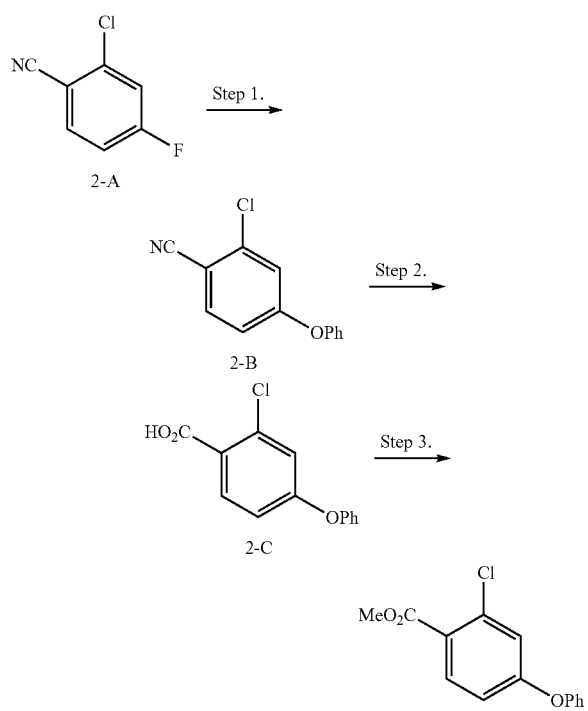

Step 1: 2-chloro-4-phenoxybenzonitrile (Intermediate 2-B)

Phenol (3.66 g, 39 mmol) dissolved in DMF (30 mL) was treated with NaH 60% dispersed in oil (1.56 g, 39 mmol) in small portions until gas evolution ceased. The reaction mixture was stirred at room temperature for 10 minutes then 2-chloro-4-fluorobenzonitrile (2-A, 5.0 g, 32.5 mmol) was added. The mixture was stirred at room temperature for 3 hours until completion (LCMS). The volatiles were removed in vacuo and the crude product was partitioned in DCM/water. The organic phase was separated and washed with a saturated brine solution, dried over Na$_2$SO$_4$. Concentration afforded 7.5 g of an off-white solid. $^1$H NMR (400 MHz, DMSO-d$_6$) δ 7.96 (d, J=8.7 Hz, 1H), 7.51 (t, J=7.9 Hz, 2H), 7.33 (d, J=7.4 Hz, 1H), 7.30 (d, J=2.3 Hz, 1H), 7.20 (d, J=7.9 Hz, 2H), 7.04 (dd, J=8.7, 2.3 Hz, 1H); MS m/z 230 [M+H]$^+$.

Step 2: 2-chloro-4-phenoxybenzoic Acid (Intermediate 2-C)

2-chloro-4-phenoxybenzonitrile (2-B, 7.0 g, 30.6 mmol), potassium hydroxide 5M (100 mL) and EtOH (20 mL) were stirred at reflux for 6 hours (until starting material was consumed). The mixture was allowed to cool to room temperature and the mixture was acidified slowly with concentrated HCl. The precipitate was filtered off and dried, giving a beige solid (2-C, 7.15 g, 94%). NMR (400 MHz, DMSO-d$_6$) δ 13.22 (s, 1H), 7.88 (d, J=8.7 Hz, 1H), 7.48 (t, J=7.8 Hz, 2H), 7.27 (t, J=7.4 Hz, 1H), 7.16 (d, J=8.0 Hz, 2H), 7.08 (d, J=2.2 Hz, 1H), 6.97 (dd, J=8.7, 2.3 Hz, 1H); MS m/z 249 [M+H]$^+$.

Step 3: methyl 2-chloro-4-phenoxybenzoate (Intermediate 2-D)

2-chloro-4-phenoxybenzoic acid (2-C, 5.0 g, 20.2 mmol) was dissolved in DMF (50 mL) and solid K$_2$CO$_3$ (4.15 g, 30.1 mmol) was added. The reaction mixture was cooled to 0° C. and methyl iodide (1.4 mL, 22.2 mmol) was added dropwise. The mixture was allowed to warm to room temperature over one hour. The starting material was all consumed within that period. The mixture was diluted with water and extracted with Et$_2$O. Drying and concentration in vacuo afforded a yellow oil (2-D, 4.15 g, 79%) which was used without further purification. NMR (400 MHz, DMSO-d$_6$) δ 7.89 (d, J=8.7 Hz, 1H), 7.49 (t, J=7.9 Hz, 2H), 7.29 (t, J=7.4 Hz, 1H), 7.17 (d, J=7.9 Hz, 2H), 7.12 (d, J=2.4 Hz, 1H), 6.99 (dd, J=8.7, 2.4 Hz, 1H), 3.84 (s, 3H); MS m/z 263 [M+H]$^+$.

Example 2: (2-chloro-4-phenoxyphenyl)(4-(((3R, 6S)-6-(hydroxymethyl)tetrahydro-2H-pyran-3-yl) amino)-7H-pyrrolo[2,3-d]pyrimidin-5-yl)methanone (Compound (I))

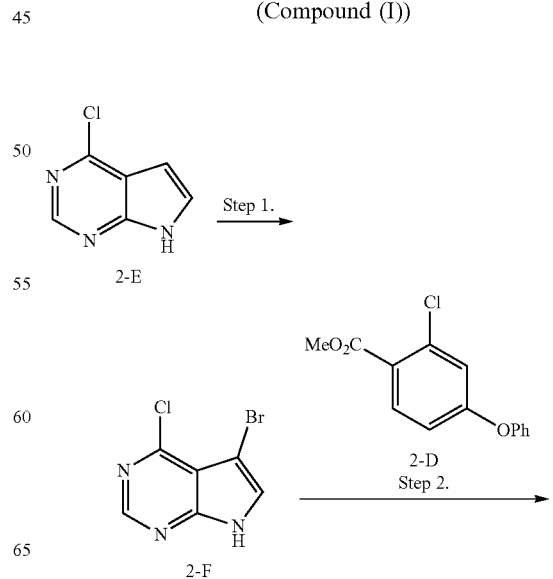

-continued

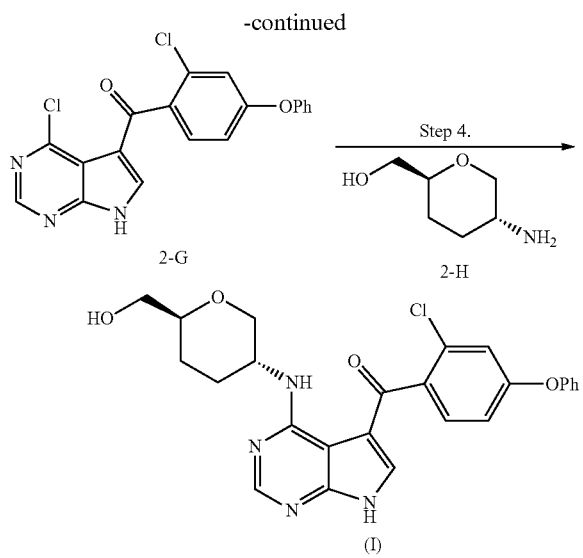

Step 1: 5-bromo-4-chloro-7H-pyrrolo[2,3-d]pyrimidine (Intermediate 2-F)

4-chloro-7H-pyrrolo[2,3-d]pyrimidine (2-E, 20.0 g, 130.7 mmol) dissolved in DCM (800 mL) was treated portion-wise with N-bromosuccinimide (26.7 g, 149.8 mmol), while maintaining the temperature around 25-30° C. The reaction mixture was stirred at room temperature overnight. Water was added (500 mL) and the phases were separated. The organic phase was dried over $Na_2SO_4$, filtered and concentrated in vacuo. The crude product was triturated in $Et_2O$ affording after filtration 5-bromo-4-chloro-7H-pyrrolo[2,3-d]pyrimidine as a white solid (2-F, 22.43 g, 74%). M.p.: 242-244° C.; $^1$H NMR (400 MHz, DMSO-$d_6$) δ 12.96 (s, 1H), 8.61 (s, 1H), 7.94 (s, 1H); MS m/z 232 [M($^{35}$Cl, $^{79}$Br)+H]$^+$, 234 [M($^{35}$Cl, $^{81}$Br)+H]$^+$, 234 [M($^{37}$Cl, $^{79}$Br)+H]$^+$, 236 [M($^{37}$Cl, $^{81}$Br)+H]$^+$.

Step 2: (2-chloro-4-phenoxyphenyl)(4-chloro-7H-pyrrolo[2,3-d]pyrimidin-5-yl)methanone (Intermediate 2-G)

To a stirred solution of 5-bromo-4-chloro-7H-pyrrolo[2,3-d]pyrimidine (2-F, 6.90 g, 29.7 mmol) in THF (200 mL) was added dropwise n-BuLi (2.69 M in hexanes, 23.2 mL, 62.3 mmol) at −78° C. under inert atmosphere. The reaction mixture was kept at −78° C. for one hour and then the pre-cooled (to −78° C.) solution of methyl 2-chloro-4-phenoxybenzoate (2-D, 8.19 g, 31.2 mmol) in THF (80 mL) was added. The reaction mixture was stirred at −78° C. for one hour then quenched with the addition of HCl 1N (65 mL). The mixture was allowed to warm to room temperature and was then extracted with EtOAc (3×100 mL). The combined extracts were washed with brine, dried over $Na_2SO_4$ and concentrated in vacuo. The crude product was purified by column chromatography ($SiO_2$, hexanes/EtOAc), giving (2-chloro-4-phenoxyphenyl)(4-chloro-7H-pyrrolo[2,3-d]pyrimidin-5-yl)methanone as a white solid (2-G, 4.73 g, 41%). $^1$H NMR (400 MHz, DMSO-$d_6$) δ 13.426 (s, 1H), 8.75 (s, 1H), 8.14 (s, 1H), 7.60 (d, J=8.5 Hz, 1H), 7.49 (t, J=7.9 Hz, 2H), 7.26 (t, J=7.4 Hz, 1H), 7.23-7.12 (m, 3H), 7.01 (dd, J=8.5, 2.3 Hz, 1H); MS m/z 384 [M($^{35}$Cl, $^{35}$Cl)+H]$^+$, 386 [M($^{35}$Cl, $^{37}$Cl)+H]$^+$, 388 [M($^{37}$Cl, $^{37}$Cl)+H]$^+$.

Step 3: (2-chloro-4-phenoxyphenyl)(4-(((3R,6S)-6-(hydroxymethyl)tetrahydro-2H-pyran-3-yl)amino)-7H-pyrrolo[2,3-d]pyrimidin-5-yl)methanone (I)

A mixture of (2-chloro-4-phenoxyphenyl)(4-chloro-7H-pyrrolo[2,3-d]pyrimidin-5-yl)methanone (2-G, 200 mg, 0.52 mmol), ((2S,5R)-5-aminotetrahydro-2H-pyran-2-yl)methanol (72 mg, 0.54 mmol) and DIPEA (272 µL, 1.56 mmol) was stirred at 160° C. for one hour under microwave irradiation. The volatiles were removed in vacuo and the residue was purified by column chromatography ($NH_2$—$SiO_2$, DCM/MeOH), giving (2-chloro-4-phenoxyphenyl)(4-(((3R,6S)-6-(hydroxymethyl)tetrahydro-2H-pyran-3-yl)amino)-7H-pyrrolo[2,3-d]pyrimidin-5-yl)methanone as an off-white solid ((I), 175 mg, 70%). $^1$H NMR (400 MHz, DMSO-$d_6$) δ 12.76 (s, 1H), 8.60 (d, J=7.1 Hz, 1H), 8.25 (s, 1H), 7.64 (s, 1H), 7.58 (d, J=8.4 Hz, 1H), 7.48 (t, J=7.6 Hz, 2H), 7.26 (t, J=7.2 Hz, 1H), 7.18-7.20 (m, 3H), 7.02 (d, J=8.3 Hz, 1H), 4.67 (s, 1H), 4.16 (d, J=7.7 Hz, 2H), 3.49-3.27 (m, 3H), 3.12 (t, J=11.2 Hz, 1H), 2.19 (d, J=11.4 Hz, 1H), 1.78 (d, J=12.9 Hz, 1H), 1.67-1.49 (m, 1H), 1.39 (d, J=12.3 Hz, 1H); MS m/z 479 [M($^{35}$Cl)+H]$^+$, 481 [M($^{37}$Cl)+H]$^+$.

Example 3: BTK Kinase Activity Assay

Test inhibitor and controls (CGI-1746, GDC-0834, PCI-32765, Dasatinib, and R-406) were prepared in 10% DMSO at 10-fold the desired final concentration, and added to each well of a reaction plate (Corning 96-well half-area solid white nonbinding surface plate) in a volume of 2.5 µl. Full-length active BTK was diluted in assay buffer (50 mM Tris, pH 8.0, 0.02 mg/ml BSA, 10 mM $MgCl_2$, 1 mM EGTA, 10% glycerol, 0.2 mM $Na_3VO_4$, 1 mM DTT, 0.1 mM β-glycerophosphate, and 0.2 mM NaF) and added to each well in a volume of 17.5 µl for a final concentration in the 25 µl reaction of 0.08 nM. After a 30 minute pre-incubation at room temperature, the kinase reaction was initiated by the addition of 5 µl of an activation mixture diluted in assay buffer containing biotinylated PLCγ2 peptide and ATP for final concentrations of 150 nM biotinylated PLCγ2 and 180 µM ATP. The plates were incubated for 60 minutes at room temperature. The reactions were stopped in the dark by the addition of 10 µl stop/detection mixture prepared in assay buffer containing EDTA and AlphaScreen™ Streptavidin Donor and anti-pTYR100 Acceptor beads. The final concentrations were 10 mM EDTA and 500 ng/well of both AlphaScreen™ donor and acceptor beads. Assay plates were incubated for 60 minutes at room temperature in the dark, and the plates were read on a Perkin Elmer Envision Multilabel plate reader (excitation wavelength: 640 nm, emission wavelength: 570 nm). The results are shown in Table 1.

Example 4: BTK C481S Kinase Activity Assay

Test inhibitors and controls (Staurosporine) were prepared in 10% DMSO at 10-fold the desired final concentration, and added to each well of a reaction plate (Corning 96-well half-area solid white nonbinding surface plate) in a volume of 2.5 µl. Full-length BTKC481S was diluted in assay buffer (50 mM Tris, pH 8.0, 0.02 mg/ml BSA, 10 mM $MgCl_2$, 1 mM EGTA, 10% glycerol, 1 mM DTT, 1 mM β-glycerophosphate, and 1 mM NaF) and added to each well in a volume of 17.5 µl for a final concentration in the 25 µl reaction of 10 nM. After a 30 minute pre-incubation at room temperature, the kinase reaction was initiated by the addition of 5 µl of an activation mixture diluted in assay buffer containing biotinylated PLCγ2 peptide, and ATP for final concentrations of 125 nM biotinylated PLCγ2, and 60 µM ATP. The plates were incubated for 60 minutes at room temperature. The reactions were stopped in the dark by the addition of 10 µl stop/detection mixture prepared in assay buffer containing EDTA, Staurosporine and AlphaScreen™ Streptavidin Donor and anti-pTYR100 Acceptor beads. The final concentrations were 15 mM EDTA, 1 µM Staurosporine and 500 ng/well of both AlphaScreen™ (Amplified Luminescent Proximity Homogeneous Assay) technology donor and acceptor beads. Assay plates were incubated for 60 minutes at room temperature in the dark, and the plates were read on a Perkin Elmer Envision Multilabel plate reader (excitation wavelength: 640 nm, emission wavelength: 570 nm). The results are shown in Table 1.

Example 5: Anti-Proliferation Assay

Cell survival was determined by the MTS assay. Briefly, cells (i.e., TMD-8 cells or Rec-1 cells) were plated in a 96-well plate at 2,000-10,000 cells per well, cultured for 24 hours in complete growth medium, and then treated with various drugs and drug combinations for 72 hours. MTS/PMS was added and incubated for 4 hour, followed by assessment of cell viability using the microplate reader (absorbance at 490 nm). Data were normalized to untreated controls and analyzed with Microsoft Excel. The results are shown in Table 1.

TABLE 1

Biological activity of Compound (I)

| BTK $IC_{50}$ (nM) | BTK (C481S) $IC_{50}$ (nM) | MTS/TMD-8 (µM) | MTS/Rec-1 (µM) |
|---|---|---|---|
| 0.5 ± 0.05 | 3.0 ± 2.4 | 0.13 ± 0.06 | 0.18 ± 0.07 |

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:

1. A method of treating cancer in a subject in need thereof, comprising
    detecting a mutant BTK in a sample from the subject;
    administering a compound of Formula (I):

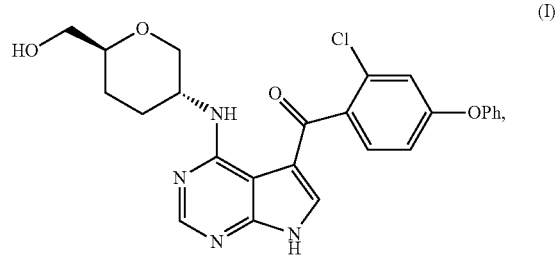 [SMILES: O=C(c1ccc(Oc2ccccc2)cc1Cl)c1c[nH]c2ncnc(N[C@@H]3CC[C@@H](CO)OC3)c12]

or a pharmaceutically acceptable salt, tautomer, or solvate, thereof, when a mutant BTK is detected wherein the mutant BTK comprises the C481 mutation.

2. The method of claim 1, wherein the cancer is resistant to a BTK inhibitor.

3. The method of claim 2, wherein the BTK inhibitor is ibrutinib.

4. The method of claim 1, wherein the cancer is selected from a cancer of the breast, ovary, cervix, prostate, testis, esophagus, larynx, stomach, skin, lung, bone, pancreas, colon, thyroid, biliary passage, hairy cells, buccal cavity, naso-pharyngeal, lip, tongue, mouth, large intestine, small intestine, colon-rectum, rectum, brain and central nervous system, bronchus, liver, intrahepatic bile duct, urinary bladder, uterine corpus, kidney, renal pelvis, oral cavity, pharynx, glioblastoma, neuroblastoma, keratoacanthoma, epidermoid carcinoma, large cell carcinoma, non-small cell lung carcinoma (NSCLC), small cell carcinoma, lung adenocarcinoma, adenoma, adenocarcinoma, follicular carcinoma, undifferentiated carcinoma, papillary carcinoma, seminoma, melanoma, sarcoma, bladder carcinoma, liver carcinoma, kidney carcinoma, myeloid disorders, lymphoma, Hodgkin's leukemia, hepatocellular cancer, glioma, endometrial cancer, multiple myeloma, acute myelogenous leukemia, chronic myelogenous leukemia, lymphocytic leukemia, chronic lymphoid leukemia (CLL), myeloid leukemia, non-Hodgkin lymphoma, and villous colon adenoma.

5. The method of claim 1, wherein the cancer is chronic lymphoid leukemia.

6. The method of claim 1, wherein the cancer is lymphoma.

7. The method of claim 6, wherein the lymphoma is non-Hodgkin lymphoma.

8. The method of claim 6, wherein the lymphoma is B-cell lymphoma.

9. The method of claim 6, wherein the lymphoma is anaplastic large cell lymphoma, central nervous system (CNS) lymphoma, or Waldenstrom macroglobulinemia.

10. The method of claim 1, wherein the cancer is myeloid disorders or myeloid leukemia.

11. The method of claim 1, wherein the cancer is acute myelogenous leukemia.

12. The method of claim 1, wherein the cancer is multiple myeloma.

13. The method of claim 1, wherein the cancer is lymphocytic leukemia.

14. The method of claim 1, wherein the cancer is sarcoma or brain tumor.

15. The method of claim 1, wherein the sample is a excited tissue or biopsy from the subject.

* * * * *